United States Patent [19]

Grögler et al.

[11] Patent Number: 4,720,545
[45] Date of Patent: Jan. 19, 1988

[54] PROCESS FOR THE PREPARATION OF COMPLEXES OF ONE MOL OF DIMERIZED OR LOW-OLIGODIMERIZED 4,4'-DIISOCYANATODIPHENYLMETHANE AND TWO TO THREE MOL OF 4,4'-DIISOCYANATODIPHENYLMETHANE, CORRESPONDING COMPLEXES, AND THEIR USE FOR POLYURETHANE PRODUCTION

[75] Inventors: Gerhard Grögler, Leverkusen; Richard Kopp, Cologne; Heinrich Hess, Leverkusen, all of Fed. Rep. of Germany

[73] Assignee: Bayer Aktiengesellschaft, Leverkusen, Fed. Rep. of Germany

[21] Appl. No.: 829,056

[22] Filed: Feb. 13, 1986

[30] Foreign Application Priority Data

Feb. 27, 1985 [DE] Fed. Rep. of Germany ....... 3506834

[51] Int. Cl.$^4$ .................. C07D 403/14; C07D 229/00
[52] U.S. Cl. .................................................. 540/202
[58] Field of Search ........................................ 540/202

[56] References Cited

U.S. PATENT DOCUMENTS

| | | | |
|---|---|---|---|
| 2,681,144 | 6/1954 | Turner | 206/72 |
| 3,290,288 | 12/1966 | Oertel et al. | 260/239 |
| 3,919,195 | 11/1975 | Bakhitov | 260/239 |
| 3,993,641 | 11/1976 | Tiemann et al. | 260/239 |
| 4,022,752 | 5/1977 | Horn et al. | 260/45.75 |
| 4,442,280 | 4/1984 | Grogler et al. | 528/54 |
| 4,521,338 | 6/1985 | Grogler | 260/239 |

FOREIGN PATENT DOCUMENTS 821158 9/1959 United Kingdom .

OTHER PUBLICATIONS

J. Org. Chem., vol. 8, pp. 17–28, (1943).

Primary Examiner—Donald G. Daus
Assistant Examiner—William A. Teoli, Jr.
Attorney, Agent, or Firm—Gene Harsh; Joseph C. Gil; Lyndanne M. Whalen

[57] ABSTRACT

The present invention relates to a process for the dimerization of 4,4'-diisocyanatodiphenylmethane from emulsion in apolar solvents with the formation of complexes and to the complexes obtainable for the first time by this process. The complexes consist of one mol of low molecular weight 4,4'-diisocyanato-diphenylmethane-uretdione or its low oligomers corresponding to the idealized formula (I)

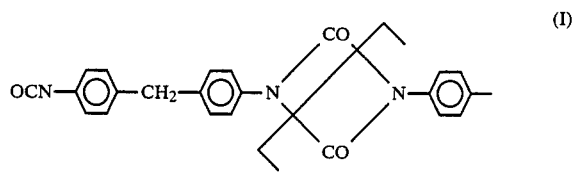
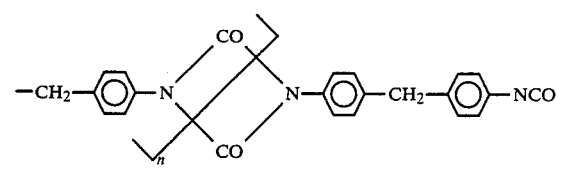

(n=0 to 0.5, where n is the average degree of oligomerization of the dimer) and 2 to 3 mol of 4,4'-diisocyanatodiphenylmethane (MDI)

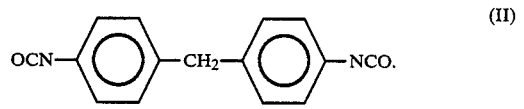

In the process according to the invention, 4,4'-diisocyanatodiphenylmethane (II) in the molten form is emulsified in apolar solvents. Dimerization is started in the presence of conventional dimerization catalysts at temperatures above the melting point of MDI, preferably up to an upper temperature limit of 50° to 60° C. The temperature is then lowered to <40° C. If desired, dimerization can be stopped when an isocyanate content of from 22.4 to 26.9% has been reached. The product is then worked up at low temperatures, preferably at 0° to 25° C. The complex obtained is claimed as a new substance. The use of the complex for the production of polyurethanes is also claimed.

10 Claims, No Drawings

PROCESS FOR THE PREPARATION OF COMPLEXES OF ONE MOL OF DIMERIZED OR LOW-OLIGODIMERIZED 4,4'-DIISOCYANATODIPHENYLMETHANE AND TWO TO THREE MOL OF 4,4'-DIISOCYANATODIPHENYLMETHANE, CORRESPONDING COMPLEXES, AND THEIR USE FOR POLYURETHANE PRODUCTION

BACKGROUND OF THE INVENTION

Aromatic uretdione-diisocyanates ("dimeric" diisocyanates) and their methods of preparation are known. See, e.g., Kunststoff-Handbuch, Volume VII, Polyurethane, published by Vieweg-Höchtlen, Carl Hanser Verlag, Munich 1966. The dimerization catalysts used in the art include not only trialkylphosphines (J. Org. Chem. 8, 23 (1943)) but also aromatic-aliphatic tertiary phosphines, alkyldiarylphosphines (German Auslegeschrift No. 2,452,390), tri- or tetra-substituted pyridines (British Pat. No. 821,158), trialkylphosphite (German Auslegeschrift No. 2,349,726) and phosphorous acid tris-dialkylamides (U.S. Pat. No. 3,290,288). The dimerization reaction to form the uretdione may in some cases take place solvent-free but solvents which are inert towards isocyanate groups are in most cases used. The following solvents, for example, are described in the art: benzene, toluene, xylene, chlorobenzene, nitrobenzene, acetone, methyl ethyl ketone, ethyl acetate, dioxane, tetrahydrofuran, aliphatic hydrocarbons, dimethylformamide and methylene chloride. No differentiation of the above-mentioned solvents according to their polarity or their power of dissolving the starting materials or products of the reaction is described in the literature noted above.

It is known that the dimerization of aromatic isocyanates, especially in the presence of reactive dimerization catalysts, may be accompanied by the formation of unwanted by-products, e.g. isocyanurate (see, e.g., U.S. Pat. No. 2,681,144). Dimerization is thus generally stopped when a desired dimerization stage has been reached. Alkylating agents such as cyclohexane sulphonic acid methyl ester or benzyl chloride, are used as inhibitors (stoppers) for the dimerization catalyst.

According to the literature cited above, aromatic diisocyanates in which the aromatic nucleus is substituted by groups R, e.g. alkyl groups, in one or both ortho-positions to the NCO group give rise to uretdione-diisocyanates having twice the molecular weight of the starting compound, e.g. the dimeric tolylene diisocyanate

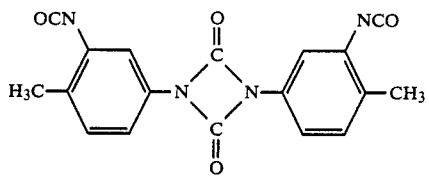

This teaching is also applied to those aromatic diisocyanates in which the aromatically bound NCO group only has hydrogen atoms in the ortho-positions. The usual term frequently used in the literature for such uretdione diisocyanates, e.g. for those based on 4,4'-diphenylmethanediisocyanate, is therefore "diphenylmethanediisocyanate dimer" or 4,4'-diisocyanatodiphenylmethane-uretdione (MDI-uretdione) or dimeric MDI, and is represented by the following formula:

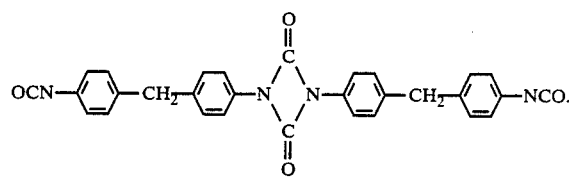

In German Auslegeschrift No. 1,445,721 (corresponding to U.S. Pat. No. 3,290,288), information was given concerning oligomeric uretdione-diisocyanate derivatives based on 4,4'-diphenylmethanediisocyanate. It is mentioned there that the dimerization of diphenylmethane diisocyanate results not only is dimeric uretdiones as end products but also in trimeric, tetrameric and pentameric uretdiones

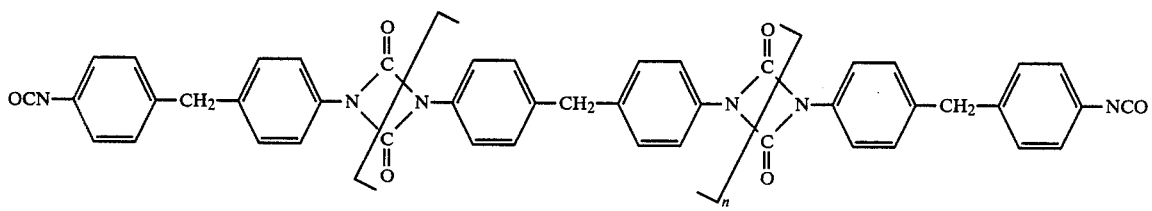

(where n=0 to 3). (See also U.S. Pat. No. 4,442,280.) "Oligomeric" dimers or uretdiones of MDI contain the uretdione group more than once in the molecule. Low-oligomeric products preferably contain this group on average n≦1 times (i.e., a maximum of two uretdione groups).

The use of dimerized diphenylmethanediisocyanate is described in German Auslegeschrift No. 2,419,968 for the synthesis of high molecular weight polyurethanes containing uretdione groups by a reaction in highly polar solvents such as DMF.

With increasing degree of oligodimerization (for example, at n>1, and in particular >2.5), however, the reactivity towards active hydrogen containing compounds markedly falls due to the decreasing solubility of these uretdione diisocyanates. Clearly, such relatively high molecular weight oligomers are no longer suitable in practice for many polyurethane reactions, especially if the reactions are carried out solvent-free or at temperatures below the (relatively high) melting points of the uretdione diisocyanates.

The importance of the solvent for the dimerization reaction is only described in a few cases in the patent literature.

Some of the inert solvents mentioned as suitable for the dimerization of aromatic isocyanates are found to be unusable for the dimerization of diphenylmethanediisocyanate since high molecular weight MDI-dimer mixtures (n>2.5) are obtained which are in most cases unsuitable for further polyurethane reactions. In very highly polar solvents (such as dimethylformamide or dimethylacetamide), the end products obtained consist almost exclusively of polydimers (n≧2.5).

The importance of the solvent for the dimerization of 4,4'-diisocyanatodiphenylmethane is disclosed in European Pat. No. 0,071,899 (corresponding to U.S. Pat. No. 4,521,338). This reference describes that the nature or quantity of the catalyst and the controlled stopping of the catalyst at a certain degree of dimerization are important to produce the desired result. The reference also describes that diphenylmethane-uretdione diisocyanates having a very low degree of oligodimerization n (n≦1, preferably ≦0.5) are obtained by using a mixture of apolar and polar solvents, especially if the apolar solvent has only a slight dissolving power for diphenylmethane-4,4'-diisocyanate (5 to 25% by weight, preferably 5 to 15% by weight). It is further described in the reference that the dimerization of 4,4'-diisocyanatodiphenylmethane in solution in an apolar solvent may also be carried out in admixture with a polar solvent. Due to the high dilution (high proportion of apolar solvent), however, this process is less economical. Furthermore, the low molecular weight diphenylmethane-uretdione diisocyanates formed still contain monomeric diphenylmethanediisocyanate starting components in a proportion of up to 20% by weight (depending on the quantity of solvent used), in most cases from 2 to 10% by weight based on the dimer (I).

DESCRIPTION OF THE INVENTION

It has now surprisingly been found that the dimerization of 4,4'-diisocyanatodiphenylmethane (MDI) results in a complex of 1 mol of low molecular weight uretdione diisocyanate (degree of oligodimerization n=0 to 0.5 in the MDI-uretdione (I)) and 2 to 3 mol of monomeric MDI, if dimerization of the MDI monomer is started, not from solution, but from an emulsion of finely divided MDI droplets in apolar solvents at temperatures above the melting point of the MDI monomer (II). It is a decided advantage of this method that only a small proportion of solvents is needed for the preparation of the emulsion. An additional advantage is that the complexes (containing about 40 to 55.5% by weight of MDI-uretdione (I)/about 60 to 44.5% by weight of MDI monomer (II), preferably 40 to 50% by weight of MDI-uretdione/60 to 50% by weight of MDI monomer) separate as solids in high yields during the dimerization reaction. Further dimerization of the MDI monomer does not take place under these operating conditions or only very slowly and can if necessary be prevented by stopping the dimerization catalyst. The complex thus obtained may advantageously be used as solid starting diisocyanate for the production of polyurethanes, and in particular for the stepwise production of polyurethanes (owing to the differing reactivities of the NCO groups in the addition compound). It is thereby possible to obtain one-component polyurethane systems which can be converted into the high-molecular weight polyurethanes from a storage-stable intermediate stage by heating. The chemical structure of the "complex" is not known. However, the complex is not a reaction product but rather is similar to a solid "crystalline complex" such as hydrates of salts.

The present invention thus relates to a process for the preparation of a novel complex formed from 1 mol of a low molecular weight 4,4'-diphenylmethane-uretdione isocyanate of the formula

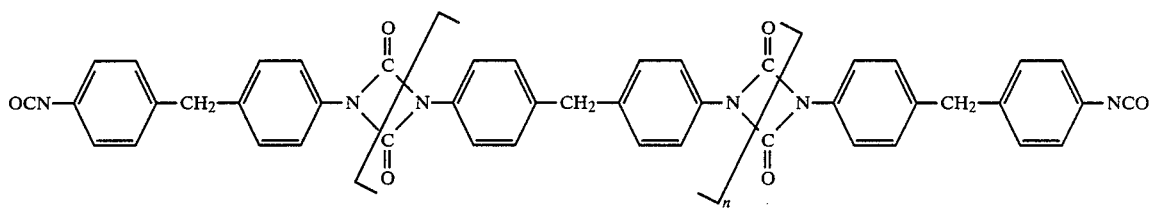

n=0 to 0.5 (n=average degree of oligodimerization) and 2 to 3 mol of

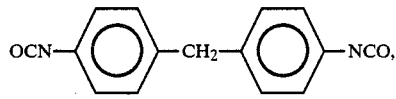

produced by the dimerization of 4,4'-diisocyanatodiphenylmethane in isocyanate-inert solvents in the presence of dimerization catalysts and optionally catalyst deactivators, characterized in that the dimerization is carried out in an emulsion of finely divided, liquid diphenylmethane-4,4'-diisocyanate in an apolar solvent as emulsifying agent, the solubility of diphenylmethanediisocyanate in said apolar solvent at room temperature being at most ≦25% by weight (preferably 2 to 15% by weight, and most preferably 2 to 12% by weight) and in that the dimerization reaction is started at or just above the melting temperature of diphenylmethane diisocyanate (e.g. 40° to 60° C. and in particular 40° to 50° C.), preferably during a time period of 5 to 100 minutes. The reaction mixture, which is initially slightly exothermic, is maintained at a temperature of 0° to <40° C. (preferably 15° to 30° C.) during the dimerization reaction or preferably is cooled to room temperature. Isolation of the complex according to the invention is preferably carried out at temperatures below 50° C., and preferably at room temperature.

The solid polyisocyanate complex prepared by the process according to the invention is an interesting starting component for polyurethanes since it contains two differingly reactive diisocyanates.

The present invention therefore also relates to the complex of 1 mol of a low molecular weight MDI uretdione diisocyanate (n=0 to 0.5) and about 2 to 3 mol of 4,4'-disocyanatodiphenylmethane, which complex has a free isocyanate content in the range of 22.4 to 26.9%, and preferably 24.4 to 26%.

The invention is also directed to the use of this complex as polyisocyanate component for the production of polyurethanes and, in particular, of storage-stable one-component polyurethane reactive mixtures.

The dimerization catalysts used for the preparation of the complex may be the usual catalysts already mentioned above but particularly preferred are trialkylphosphines such as triethylphosphine or tributylphosphine. The catalysts are used in the usual quantities, e.g. from 0.05 to 5% by weight, preferably from 0.1 to 1.0% by weight and most preferably from 0.1 to 0.35% by weight.

Suitable "apolar" emulsifying media are those compounds which have as low as possible a dissolving power for the starting component MDI. These are generally aliphatic and/or cycloaliphatic hydrocarbons such as hexane, octane, cyclopentane or cyclododecane or corresponding hydrocarbon distillates containing predominantly aliphatic and/or cycloaliphatic hydrocarbons, e.g. petroleum ethers, gasoline of the kind used for cleaning, or ligroin. The dielectric constant of such solvents is generally below 2.10.

Emulsifying media ("solvents") containing an ether group in the molecule are also suitable. Examples include di-n-propylether, diisopropylether, methyl tert.-butylether and methyl tert.-amylether, and especially diisopropylether.

To carry out the process according to the invention, the starting component MDI is added in molten form to the emulsifying agent ("solvent") which is at a temperature above the melting point of MDI.

Satisfactory preparation of the MDI emulsion generally requires vigorous mixing of the two liquid phases (mechanical stirrer). Known emulsifying agents may be used in addition to the necesary "solvent". Alternatively, a mixture of powdered MDI and the apolar solvent may be heated to temperatures above the melting point of MDI with vigorous stirring. The dimerization catalyst is then added to the emulsion.

Dimerization is started at temperatures above the melting point of MDI, e.g. at 40° to 60° C., in particular at 40° to 50° C. within a relatively short time of 5–100 minutes, preferably 5–30 minutes. The reaction mixture is then maintained at a temperature of 0° to at the most 40° C., and preferably at 15° to 30° C. Most preferably, the reaction mixture is cooled to room temperature. Under these conditions, the dimerization reaction takes about 1 to 6 hours.

Although a larger quantity of solid adduct is obtained within a shorter reaction time if a temperature above 40° C. is maintained during the whole dimerization reaction, the products obtained under these conditions sometimes have lower isocyanate contents, depending on the choice of solvent (emulsifying agent) (i.e. an increasing degree of oligodimerization, with values of $n \geq 0.5$). Isocyanate contents below the limit claimed according to the invention may result.

The quantity of emulsifying agent (solvent) may vary within wide limits but it is advantageous to use smaller quantities of emulsifying agent if it has a relatively good dissolving power for MDI (e.g. more than 10% by weight MDI in the solution at room temperature). The quantity of emulsifying agent must, of course, be chosen so that the solid suspension of addition compound obtained from the emulsion by dimerization remains stirrable. This also facilitates isolation of the complex, e.g. by filtration. The weight ratio of emulsifying agent to MDI is generally from 1 to 5:1 and preferably from 2 to 3:1.

Suitable deactivators for the dimerization are known and can be used, if desired.

Precipitation of the complex begins shortly after addition of the catalyst if the above-mentioned reaction temperatures are employed.

Successive removal of samples shows that a complex invariably separates from the emulsion at the beginning of the dimerization reaction, even when a large excess of MDI is used. No further dimerization of the MDI monomer in the complex takes place under these operating conditions (low temperature, e.g. room temperature). It is nevertheless advisable to stop the reaction when dimerization has terminated, especially if the emulsifying agent has a "relatively good" dissolving power for MDI monomers (e.g. $\geq 10\%$ dissolved MDI).

A specific complex of 1 mol of low molecular weight MDI dimer (I; n=0) and 2 mol of MDI (50% by weight MDI dimer, 50% by weight MDI) is calculated to have an insocyanate content of 25.2% by weight of free NCO. A specific complex of the same MDI dimer and 3 mol of MDI (II) is calculated to have a free isocyanate content of 26.9%. The values found in practice, however, may occasionally be somewhat higher since the low molecular weight MDI dimer (for MDI dimer (I) with n=0, the free isocyanate content is calculated to be 16.8%) may include additional monomeric MDI depending in particular on the choice of solvent. This proportion of additional monomeric MDI may be as much as about 20% by weight of additional free MDI, based on the MDI dimer, preferably up to 10% by weight, so that the NCO content of the dimer may be increased to 19.6% or 18.3%, respectively.

This form of inclusion of monomeric MDI to an extent of 10 to 20% by weight in the dimerized MDI occurs in the state of the art dimerization reactions, i.e. dimerization from a solution of MDI, and can only be extracted with difficulty by 30 minutes' treatment with toluene at 50° to 60° C. The process according to the invention of the dimerization reaction from emulsion therefore also occasionally results in complexes of MDI dimer (I) and MDI in which the isocyanate contents are slightly raised (up to 27% by weight, see Examples).

Complexes having an isocyanate content below 22.4% NCO (corresponding to a dimer (I) having a free isocyanate content below 13.44%) are hardly suitable for the use according to the invention as polyurethane components. Such complexes contain much more highly oligomeric MDI-uretdione ($n > 0.5$) which is very difficult to react with active hydrogen containing compounds due to its low solubility. Such complexes in which the isocyanate content is too low are formed when polar solvents are used as emulsifying agents or when the reaction temperature is too high or when the reaction time in polar solvents is too long before the dimerization reaction is stopped.

Only mild temperature conditions should therefore also be observed at the stage of working up the complex of the invention because otherwise uretdione formation would continue due to reaction of the free NCO groups of the dimeric MDI and the NCO groups of monomeric MDI and polymeric uretdiones (I; $n > 0.5$) would be produced. The latter are extremely difficult to dissolve, in particular when $n \geq 1$, and contain only few free NCO groups and are extremely difficult to react further. This could be the reason for the failure hitherto to use so-called "dimers" of diphenylmethane-4,4'-diisocyanate, since these "dimers" obtained by the methods hitherto employed could only be obtained in a polymeric or highly oligomerized form (and not in a truly dimeric or only slightly oligomerized form (n≦0.5)).

The complex according to the invention may advantageously be used for the production of polyurethane systems. It is suitable in particular for the preparation of one-component reactive systems as described in German Offenlegungsschriften Nos. 3,230,757 and 3,419,429.

The relatively high molecular weight compounds containing Zerewitinoff-active hydrogen atoms described in the art may be used as conventional polyurethane starting components. Particularly useful are polyols and/or polyamines. Optionally, other polyisocyanates, low molecular weight chain lengthening agents or cross-linking agents (in particular water, diols and/or aromatic diamines), and the usual additives, auxiliary agents and catalysts may also be used. The usual, well-known, one-shot or multistage processes are suitable for preparing the polyurethanes. In particular, the complexes may also be used in a form of one-component reactive systems since the monomeric MDI component initially leads to relatively high molecular weight polyurethanes, which in turn do not react further to form the polyurethane end products until they are heated with the dimers.

A comprehensive list of suitable starting materials, such as relatively high molecular weight active hydrogen containing compounds, chain lengthening agents and cross-linking agents and optional additional diisocyanates and additives is described in German Offenlegungsschriften Nos. 2,854,384, 2,920,501, and 3,230,757 and European Pat. No. 71,139.

The invention is further illustrated, but is not intended to be limited by the following examples in which all parts and percentages are by weight unless otherwise specified.

EXAMPLES

Example 1

Determination of the solubility of 4,4'-diisocyanatodiphenylmethane (MDI) (Preliminary experiments)

The solubility of MDI in some apolar solvents was determined at room temperature (25° C.) and at 40° C. by NCO titration. 100 g of solvent and 50 g of MDI were mixed at the given temperature for ½ hour with stirring. The mixture obtained was filtered or decanted and the isocyanate content of the clear solution was determined. The concentration of MDI in the apolar solvent is obtained from the isocyanate content.

| Solvent | at room temperature | | at 40° C. NCO content % | MDI g/100 g solvent |
|---|---|---|---|---|
| | NCO content % | MDI g/100 g solvent | | |
| Petroleum ether | 3.75 | 11.2 | 9.6 | 28.6 |
| Cleaning gasoline | 3.95 | 11.8 | 7.0 | 20.8 |
| Hexane | 4.0 | 11.9 | 11.8 | 35.1 |
| Ligroin | 6.1 | 18.2 | 11.1 | 33.0 |
| Cyclohexane | 7.05 | 21.0 | 9.95 | 29.6 |
| Diisopropylether | 10.2 | 30.4 | 11.4 | 32.9 |

Example 2

(a) Dimerization of MDI in apolar and polar solvents (according to the invention and comparison)

100 g of the given solvents are heated to 40° C. and mixed with 50 g of molten MDI (m.pt.: 40° to 45° C.) with stirring. 0.3 g of tributyl phosphine are then added and the heating is removed. Crystalline separation of the solid, dimer-containing MDI complex is observed within a short time. Stirring of the reaction mixture is continued for 4 hours, during which the temperature slowly falls from 30° to 20° C. The solid precipitate is suction filtered, washed with a little solvent and dried in a vacuum at 40° to 50° C. The isocyanate content of the sample is then determined.

| No. | Solvent | | Yield % of theoretical | Titration isocyanate content % | |
|---|---|---|---|---|---|
| 1 | Petroleum ether | slightly polar solvents; according to the invention | 95 | 26.5 | |
| 2 | Gasoline for cleaning | | 90 | 25.9 | |
| 3 | Hexane | | 86 | 25.8 | |
| 4 | Ligroin | | 94 | 26.0 | |
| 5 | Cyclohexane | | 94 | 25.7 | |
| 6 | Diisopropylether | | 92 | 24.8 | |
| 7 | Chlorobenzene | polar solvents (for comparison, not according to the invention) | 92 | 17.8 | |
| 8 | Ethyl acetate | | 90 | 14.5 | partly insoluble |
| 9 | Methyl glycol ether acetate | | 94 | 18.1 | |
| 10 | Benzonitrile | | 96 | 13.5 | partly insoluble |
| 11 | Acetone | | 95 | 14.5 | partly insoluble |

Whereas dimerization of MDI in admixture with the apolar solvents to be used according to the invention results in a complex having an isocyanate content of from 24.8 to 26.5 (see 1 to 6), the reaction carried out under the same conditions in polar solvents results in part in relatively high molecular weight dimeric MDI oligomers having values of n>0.5 or >1.0 (see 7 to 11). In contrast to the result obtained with apolar solvents, MDI is readily soluble in the above-mentioned polar solvents so that relatively highly oligomeric dimerization products are liable to be obtained but not the complexes according to the invention. Similarly (highly) diluted solutions (instead of—more concentrated—emulsions) of MDI in apolar solvents also given rise to relatively highly oligomeric uretdione products but not to the complexes.

Progress of the dimerization reaction of MDI from emulsions in apolar solvents 250 g (1.0 mol of molten MDI were added to 500 ml of the given solvent at 40° C. with vigorous stirring. 0.5 g of tributylphosphine were then added and the heating means removed. The temperature stayed at 35° to 40° C. for some time due to the slightly exothermic reaction but gradually fell to room temperature (20° to 25° C.). 50 ml samples of the resulting suspension were removed at hourly intervals. The dimerization catalyst was inactivated with a few drops of ethyl toluene sulphonate and the solid was suction filtered, washed and dried at low temperatures. The weight and isocyanate content of these solid samples were then determined.

After a reaction time of 6 hours, dimerization was stopped in the whole reaction mixture by the addition of 0.5 g of ethyl toluene sulphonate (tosyl ester) and the mixture was worked up after it had been stored overnight (Method A).

In another test series in the said solvents, the reaction mixture was not stopped with tosyl ester but was otherwise examined as in the above series and under the same conditions (Method B).

In addition, the MDI dimer was isolated from Method A by extraction with toluene (½ hour/60° C.) and the isocyanate content was determined by titration (C).

ning of the dimerization reaction and when a high proportion of MDI dimer and relatively low proportion of MDI is preset at the end of the dimerization reaction. Extraction with toluene (½ hour/60° C.) followed by isolation of the insoluble dimer content shows that MDI dimers which in part have a slightly raised isocyanate content have been formed in the stated solvents (e.g. hexane, petroleum ether). It may be assumed that unextractable but still titratable MDI is enclosed in the product to an extent of the order of up to 20% by weight. In the complexes, of 2 to 3 mol of MDI, the raised isocyanate content of the dimeric MDI also appears in the final balance so that these complexes also contain titratable MDI in the same amount (i.e., up to 20% by weight).

It is also clear from the examples that in certain solvents (e.g. hexane), interruption of dimerization (by the addition of the usual reaction stoppers, e.g. tosyl ester) leads to specific complexes. It is for this reason that stopping of dimerization may be preferable.

Example 3

Dimerization of MDI at elevated temperature

In contrast to the experiments described in Example 2, in which the reaction was started at 40° C. and then continued at room temperature (20° to 25° C.), the dimerization of MDI was in this case carried out at 40° C. throughout. The "solvent" used was petroleum ether

| | Apolar solvent | | | | | | | | |
|---|---|---|---|---|---|---|---|---|---|
| Removal of sample after h | Hexane g of solids/NCO % | | Cyclohexane g of solids/NCO % | | Petroleum ether g of solids/NCO % | | Ligroin g of solids/NCO % | | Diisopropyl ether g of solids/NCO % |
| 1 | 4.1 | (27.3) | 5.9 | 26.5 | 4.6 | (27.4) | 5.6 | 26.5 | 2.7 | 27.0 |
| 2 | 7.9 | 26.7 | 6.3 | 25.8 | 5.5 | 27.0 | 6.8 | 26.9 | 4.8 | 26.5 |
| 3 | 8.2 | 26.5 | 8.2 | 25.7 | 6.7 | 26.5 | 7.8 | 25.0 | 5.5 | 26.1 |
| 4 | 8.7 | 26.9 | 8.3 | 25.3 | 8.3 | 26.5 | 8.8 | 26.0 | 6.1 | 26.4 |
| 5 | 9.3 | 25.3 | 8.8 | 26.0 | 8.2 | 26.5 | 9.2 | 25.5 | 6.2 | 25.9 |
| 6 | 10.0 | 25.6 | 11.0 | 25.5 | 8.5 | 26.8 | 9.7 | 25.6 | 6.4 | 25.8 |

| Removal of sample after 6 hours | Hexane g of solids/NCO % | Cyclohexane g of solids/NCO % | Petroleum ether g of solids/NCO % | Ligroin g of solids/NCO % | Diisopropyl ether g of solids/NCO % |
|---|---|---|---|---|---|
| | Method A: (Dimerization interrupted) | | | | |
| Yield in g in % of theoretical | 200 g/25.2 (88%) | 215 g/25.2 (86%) | 215 g/26.7 (86%) | 212 g/25.2 (85%) | 205 g/24.8 (82%) |
| | MDI dimer (C) (extracted from A) | | | | |
| % NCO | 17.2 | not measured | 17.8 | 16.8 | 16.9 |
| | Method B: (Dimerization not interrupted) | | | | |
| Yield in g in % of theoretical | 210 g/24.5 (84%) | 205 g/24.8 (82%) | 202 g/25.8 (81%) | 200 g/25.0 (80%) | 190 g/24.5 (76%) |

The result shows that a complex having an isocyanate content of from 24.4 to 27% (NCO calculated for 1 mol of dimer and 2 mols of MDI=25.2%; for 1 mol of dimer and 3 mols of MDI=26.9%) is invariably formed both when a very large excess of MDI is present at the beginning and ligroin. The reaction mixtures were worked up (removal of sample, isolation of addition product, extraction) as in Example 2.

| | Petroleum ether | | Ligroin | |
|---|---|---|---|---|
| Sample after h | g of solids/50 ml | % NCO | g of solids/50 ml | % NCO |
| 2 | 10.0 | 27.2 | 5.0 | 25.8 |
| 3 | 10.2 | 27.1 | 6.2 | 25.1 |
| 4 | 11.2 | 26.8 | 9.1 | 24.2 |
| 5 | 10.8 | 26.4 | 8.8 | 22.8 |
| 6 | 11.2 | 26.6 | 8.5 | 22.2* |
| Extraction of addition product | | 17.8 | | 12.0* |

| | Petroleum ether | | Ligroin | |
|---|---|---|---|---|
| Sample after h | g of solids/50 ml | % NCO | g of solids/50 ml | % NCO |
| after 6 h | | | | |

*in part insoluble when attempts are made at titration (not according to the invention)

Whereas the dimerization of MDI in petroleum ether at 40° C. still leads to a definite addition compound having an NCO content of 26.6% (after extraction, NCO content=17.8% in the dimer (I)), the compound obtained in ligroin at a continuous dimerization temperature of 40° C. is unsuitable in practice for further polyurethane reactions by the process according to the invention. The MDI dimer is then already present in a too high molecular weight form (n>>0.5; free NCO=12%) and can no longer be satisfactorily and completely reacted with the usual active hydrogen compounds due to its low solubility. The dimerization reaction from emulsion to prepare the complex according to the invention which is started at 40° to 60° C., is then preferably continued at lower temperatures (preferably room temperature) in the later stage to eliminate the possibility of excessive oligodimerization (e.g. n>0.5). The most suitable dimerization temperature can easily be determined by suitable preliminary tests in the selected solvent.

Example 4

Characterization of the complex according to the invention

The isocyanate content of the complex of 1 mol of MDI dimer (I; n=0 to n=0.5) and 2 to 3 mol of MDI is in the range of 22.4 to 26.9% free NCO (calculated value from 25.2% to 26.9% free NCO).

On titration with di-n-butylamine in acetone at room temperature, the complexes according to the invention form a clear solution. The bands for NCO (2250 cm$^{-1}$) and uretdione (1780 cm$^{-1}$) are clearly visible in the IR spectrum.

As the following experiment shows, the MDI monomer can easily be extracted from the complex by means of polar solvents, especially in the heat. A low molecular weight MDI dimer is left as residue.

Conditions for extraction:
  100 g of toluene
  20 g of a complex of 1 mol of dimer and 2 mols of MDI (NCO 25.3%)
  30 min/60° C.
  Residue/solid: 9.8 g; NCO=16.8% (calculated MDI dimer 16.8% at n=0)
  Filtrate concentrated by evaporation: 10.2 g; NCO 32.8% (calculated MDI 33.6%)

Proportions: $\frac{\text{Dimer(mol 500)}}{\text{MDI mol 250}} = \frac{9.8}{10.2} = \frac{19.6 \text{ mMol}}{40.8 \text{ mMol}} = \frac{1}{2.08}$ At the usual rate of heating up for determining the melting point of the complex according to the invention, slight sintering of the compound in the region of 40° to 45° C. (m.pt. of MDI) can be seen only in a few cases. Gradual decomposition of the product sets in above 250° C. The absence of a clear melting range at 40° to 45° C. could be explained on the grounds that the MDI present with the MDI dimer in the complex is continuously converted into higher molecular oligomers at elevated temperatures. If, for example, a sample of complex is kept for a considerable time at 120° C., then a marked drop in NCO occurs and an insoluble, relatively highly oligomeric MDI dimer is obtained after some hours.

Conversion of the complex into oligo dimers (II) (n>>0.5) by tempering at 120° C.:

| Time/h | % NCO | |
|---|---|---|
| 0 | 25.3 | |
| 1 | 24.8 | |
| 2 | 23.4 | |
| 5 | 18.5 | |
| 10 | 12.1 | insoluble constituents |
| 13 | 10.7 | on titration |

Due to this conversion by heat, the complex is worked up at the lowest possible temperatures (e.g. 0° to 40° C., preferably 0° to 25° C.).

Example 5

Preparation of the complex according to the invention 1000 g of molten MDI (40° to 45° C.) were introduced with vigorous stirring into 2000 ml of hexane which had been heated to 40° C. 1.5 g of tributylphosphine was then added to the MDI/hexane emulsion obtained. The heating means were then removed. The complex began to separate in the form of small crystals shortly after addition of the dimerization catalyst (a few minutes). Stirring was continued for a further 5 hours, during which the reaction temperature gradually fell from 30° to 25° C. Dimerization was then stopped with 1.5 g of tosyl ester. The reaction mixture was left to stand at room temperature for several hours to ensure complete separation of the compound. The solid material was then separated by suction filtration and washed with a little hexane. The residue was then dried in a vacuum at 30° to 50° C. 940 g (94% of theoretical) of the solid complex were obtained: isocyanate content 25.4% (calculated 25.2% for 1:2) and a decomposition point above 250° C.

Even if the dimerization catalyst is not deactivated, dimerization results in a definite compound since further dimerization is prevented by precipitation due to the low solubility of the dimerized compound in hexane.

Example 6

Polyurethane/2-stage synthesis/polyether 160 g of complex having an isocyanate content of 26.2% were added to a mixture of 500 g (0.25 mol) of a linear polypropyleneglycolether (molecular weight 2000, OH number 56) 44.5 g (0.25 mol) of 2,4- and 2,6-diamino-3,5-diethyltoluene mixture (in a molar ratio of 65/35) (DEDTA) and 0.5 g of lead octoate (50% solution in petroleum hydrocarbons) and the mixture was stirred until homogeneous. A preliminary reaction of the aromatic diamine DEDTA took place after a short time at room temperature, mainly with the MDI present in the complex (exothermic). A tough-plastic polyurethane prepolymer was obtained after a few hours at room temperature. At this stage of addition, practically only MDI monomer entered into the reaction while the MDI dimer, which is slower to react due to its low solubility, remained as inert polyisocyanate in the presence of the polyether and only reacted at elevated temperatures and in the presence of catalyst (lead octoate). The final strengthening of the tough-plastic prepolymer was therefore not achieved until a reaction temperature of 120° to 130° C. was employed. This strengthening of the prepolymer may be carried out either immediately after its preparation or at any time thereafter, under pressure and with shaping. The product obtained after the final strengthening was an elastic, stiff polyurethane material having a hardness of 90 to 95 A.

Example 7

Polyurethane/2-stage synthesis/polyester 43.3 g (0.24 mol) of 2,4- and 2,6-diamino-3,5-diethyl-toluene (isomeric mixture 65/35), 0.1 g of lead octoate (solution) and 0.1 g of FORMREZ UL 29 (S-containing Sn catalyst, Witco/USA) were stirred into a melt (about 50° to 60° C.) of 200 g (0.1 mol) of a linear polyester of adipic acid and ethylene glycol having a molecular weight of 2000 (OH number 56), followed by 114.9 g of the complex, 26% NCO) and the contents were rapidly mixed. The preliminary reaction of the aromatic diamine with the MDI present in the complex took place after a short time in the polyester melt. After cooling of the melt to room temperature, a solid but brittle and breakable prepolymer which was indefinitely stable in storage at room temperature was obtained. At this stage of addition, the aromatic diamine (0.24 mol) only reacted with the MDI present (0.24 mol) without participation of the MDI dimer.

The solid prepolymer can be granulated with the aid of suitable grinding apparatus. The granulate may be solidified to an elastic, stiff polyurethane material with a hardness of 95 A, either immediately or at any time thereafter, at a reaction temperature of 120° to 140° C. under pressure and with shaping. Polyaddition of the MDI dimer with the higher melting polyester (m.pt. about 50° C.) took place at this phase of solidification at elevated temperature and with the aid of catalysts. An elastomer with advantageous properties was obtained.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. In a process for the preparation of a complex by the dimerization of 4,4'-diisocyanatodiphenylmethane in isocyanate-inert solvents in the presence of dimerization catalysts and optionally reaction stoppers, wherein the improvement comprises dimerization in an emulsion of finely divided, liquid diphenylmethane-4,4'-diisocyanate in an apolar solvent as emulsifying agent, the solubility of diphenylmethanediisocyanate at room temperature in said apolar solvent being at the most 25% by weight, and wherein the dimerization reaction is started at or slightly above the melting temperature of diphenylmethanediisocyanate and the reaction mixture, which initially is slightly exothermic, is kept at a temperature of 0° to 40° C. during dimerization.

2. The process of claim 1, wherein said solubility is from 2 to 15% by weight.

3. The process of claim 2, wherein said solubility is from 2 to 12% by weight.

4. The process of claim 1, wherein the dimerization is started at a temperature of from 40° to 60° C.

5. The process of claim 4, wherein the dimerization is started at a temperature of from 40° to 50° C.

6. The process of claim 1, wherein the reaction mixture is kept at a temperature of from 15° to 30° C. during dimerization.

7. The process of claim 1, wherein the reaction mixture is cooled to room temperature during dimerization.

8. A complex formed from 1 mol of a low molecular weight MDI-uretdione diisocyanate of the formula

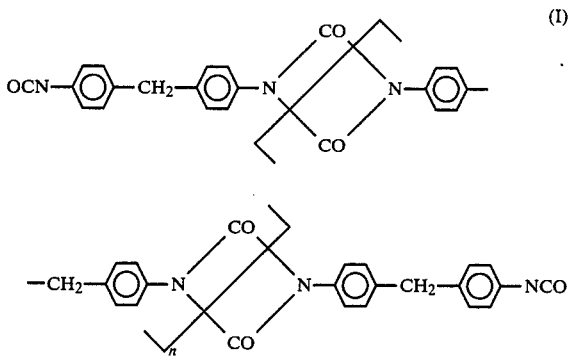

(I)

where n=0 to 0.5, and from about 2 to 3 mol of 4,4'-diisocyanatodiphenylmethane, the free isocyanate content of said complex being in the range of 22.4 to 26.9% by weight.

9. The complex of claim 8 having a free isocyanate content of from 24.4 to 26% by weight.

10. In the process for the production of a polyisocyanate addition product by reacting an isocyanate with an active hydrogen containing compound, the improvement wherein said isocyanate comprises the complex of claim 8.

* * * * *